(12) United States Patent
Jiang et al.

(10) Patent No.: US 10,527,542 B2
(45) Date of Patent: Jan. 7, 2020

(54) METHOD OF CALCULATING TAVI BASED ON A BAND RATIO MODEL AND SOLAR ALTITUDE ANGLE

(71) Applicant: Fuzhou University, Minhou Fuzhou (CN)

(72) Inventors: Hong Jiang, Minhou Fuzhou (CN); Xiaoqin Wang, Minhou Fuzhou (CN); Chongcheng Chen, Minhou Fuzhou (CN)

(73) Assignee: Fuzhou University, Minhou Fuzhou (CN)

( * ) Notice: Subject to any disclaimer, the term of this patent is extended or adjusted under 35 U.S.C. 154(b) by 64 days.

(21) Appl. No.: 15/740,011

(22) PCT Filed: Mar. 19, 2017

(86) PCT No.: PCT/CN2017/076022
§ 371 (c)(1),
(2) Date: Dec. 27, 2017

(87) PCT Pub. No.: WO2018/028191
PCT Pub. Date: Feb. 15, 2018

(65) Prior Publication Data
US 2018/0356339 A1  Dec. 13, 2018

(30) Foreign Application Priority Data

Aug. 10, 2016 (CN) .......................... 2016 1 06484178
Dec. 9, 2016 (CN) .......................... 2016 1 11274610

(51) Int. Cl.
*G06K 9/00* (2006.01)
*G01N 21/17* (2006.01)
(Continued)

(52) U.S. Cl.
CPC ....... *G01N 21/3563* (2013.01); *G01N 21/359* (2013.01); *G06K 9/00657* (2013.01);
(Continued)

(58) Field of Classification Search
CPC ............ G01N 21/3563; G01N 21/359; G01N 2021/1793; G01N 2021/1797; G06K 9/00657
See application file for complete search history.

(56) References Cited

U.S. PATENT DOCUMENTS 5,764,819 A * 6/1998 Orr ...................... G06K 9/0063
382/110
7,068,816 B1   6/2006 Knoblauch et al.
(Continued)

FOREIGN PATENT DOCUMENTS

CN      101561502 A     10/2009
CN      101825702 A     9/2010
(Continued)

OTHER PUBLICATIONS

Tang et al. "Normalization of Sun/View Angle Effects in Vegetation Index using BRDF of Typical Crops." IEEE International Geoscience and Remote Sensing Symposium, Sep. 20, 2004, pp. 4063-4065 (Year: 2004).*
(Continued)

*Primary Examiner* — Jon Chang
(74) *Attorney, Agent, or Firm* — Luoh J. Wu; Continent Patent Office LLP

(57) ABSTRACT

The present invention relates to a method of calculating a Topography Adjusted Vegetation Index (TAVI) based on a band ratio model and a solar altitude angle. The method includes the following steps: obtaining the apparent reflectance data of a remote sensing image through image pre-
(Continued)

processing, analyzing the quality of the image and numerical distribution, calculating a Shadow Vegetation Index (SVI), and constructing a TAVI combinational algorithm:

$$TAVI = \frac{B_{ir}}{B_r} + f(\Delta) \cdot \frac{1}{B_r},$$

calculating an adjustment factor $f(\Delta)$ with the solar altitude angle, and finally obtaining anti-topographic effect TAVI vegetation information. The TAVI in the present invention is composed of two band ratio submodels RVI and SVI, the denominators of both of which are red band data of a remote sensing image, and the adjustment factor $f(\Delta)$, which is calculated by a solar altitude angle as a parameter with a sensor factor applied, has great physical significance. The TAVI calculation method does not need digital elevation model (DEM) data and remote sensing image classification when not depending on ground survey data, and ensures that the interference of the topographic effects with the vegetation information can be effectively eliminated by the TAVI, thereby avoiding the problem of reduced inversion accuracy of ground vegetation information due to different registration accuracy of a remote sensing image and DEM data.

4 Claims, 1 Drawing Sheet

(51) Int. Cl.
  *G01N 21/3563* (2014.01)
  *G01N 21/359* (2014.01)

(52) U.S. Cl.
  CPC ............. *G01N 2021/1793* (2013.01); *G01N 2021/1797* (2013.01)

(56) References Cited

U.S. PATENT DOCUMENTS

2011/0135197 A1* 6/2011 Paris ............... G06T 7/00
   382/165
2016/0300375 A1* 10/2016 Beckett ............ G06T 3/4092

FOREIGN PATENT DOCUMENTS

| CN | 104142142 A | 11/2014 |
| CN | 105487066 A | 4/2016 |
| CN | 106324614 A | 1/2017 |

OTHER PUBLICATIONS

Anvar et al. "A New Method to Reduce the Sun Angle Effects and Noise Contamination in Extracting the Vegetation Indices from Satellite Images." IEEE International Geoscience and Remote Sensing Symposium, Jul. 23, 2007, pp. 1909-1914 (Year: 2007).*
Jiang et al. "Vegetation Monitoring in Rugged Terrain with One Novel Topography-Adjusted Vegetation Index (TAVI)." 3rd International Congress on Image and Signal Processing, Oct. 16, 2010, pp. 2294-2297 (Year: 2010).*
Jiang et al. "Developing a Novel Topography-Adjusted Vegetation Index (TAVI) for Rugged Area." IEEE International Geoscience and Remote Sensing Symposium, Jul. 25, 2010, pp. 2075-2078 (Year: 2010).*
Kusaka et al. "Correction of Topographic Effects for the Vegetation Index Obtained from NOMAVHRR Data." IEEE International Geoscience and Remote Sensing Symposium, Jul. 24, 2000, pp. 837-839 (Year: 2000).*

* cited by examiner

METHOD OF CALCULATING TAVI BASED ON A BAND RATIO MODEL AND SOLAR ALTITUDE ANGLE

BACKGROUND OF THE INVENTION

1. Technical Field

The present invention relates to a method of calculating a TAVI based on a band ratio model and a solar altitude angle.

2. Description of Related Art

In a complex topographic mountainous area, the solar radiation distribution on the surface of the mountainous area may change under topographic effects, so that the radiance value of a mountain's shady slope area of a remote sensing image decreases while the radiance value of a sunny slope area increases, leading to severe problems such as "the same object with different spectra" and "the same spectrum with different objects". The accuracy of the inversion of the relevant biological parameters of a mountain's vegetation by a conventional remote sensing method for the vegetation index may be reduced accordingly. Therefore, diluting the topographic effects has become an important problem confronting the remote sensing of vegetation in complex topographic mountainous areas.

The following are currently major correction ideas and models:

(I) Experiential statistical models. Such models mainly include a cosine model, a C correction model, an SCS model, an SCS+C model, a Proy mode, a Minnaert model, and the like. These methods mainly provide correction of direct solar radiation at the bands of a remote sensing image by using digital elevation model (DEM) data to reduce the difference in radiance between a mountain's shady slope and sunny slope with good results. However, these methods may have a problem of overcorrection because the effects of atmospheric scattered radiation and adjacent topography reflected radiation are not taken into account. Moreover, the promoted application of such method within a large range is restricted due to such problems as accuracy and availability (such as security restrictions, long data update cycle, and the like) of high-accuracy DEM data, registration accuracy between DEM and a remote sensing image.

(II) Mountainous radiation transfer models. Such models are physical models based on a radiation transfer theory, which allow topographic correction through a physical process of studying light-surface interaction in conjunction with DEM data. Such a method can eliminate the effects of direct solar radiation, atmospheric scattered radiation and adjacent topography reflected radiation in a remote sensing image due to complex topography in theory, but promoted application of the models is restricted by complex model parameters and great difficulty in obtaining desired parameter data.

(III) Wave ratio models. Such models may directly generate vegetation index information that is not affected or less affected by the topography mainly by performing calculations such as division on the bands of a remote sensing image. Such models have no requirement on additional input data and are a special vegetation index to a particular extent, but are unstable in application results. Therefore, their stability and results should be further improved for large-area promoted application.

Topography Adjusted Vegetation Index (TAVI) is a special band ratio model, which, in an existing proposed algorithm, includes two important components, i.e., a combinational algorithm and an adjustment factor $f(\Delta)$, where the TAVI combinational algorithm is shown by a formula (2-1):

$$TAVI = CVI + f(\Delta) \cdot SVI \quad (2\text{-}1)$$

$$SVI = \frac{M_r - B_r}{B_r} \quad (2\text{-}2)$$

In the formula, CVI is a conventional vegetation index, such as a Normalized Difference Vegetation Index (NDVI), a Ratio Vegetation Index (RVI) and the like; SVI is a shadow vegetation index, where $B_r$ represents red-band data of a remote sensing image, and $M_r$ represents the maximum of the red-band data; and $f(\Delta)$ is the adjustment factor.

With regard to the combinational algorithm, due to a great number of CVIs, confusion may be easily caused in the absence of a uniform standard for which a special vegetation index is selected during practical application. The numerator of the SVI algorithm is a variable, resulting in instability of the SVI calculation results. Therefore, the existing combination form of the RVI and SVI has great uncertainty, which affects the large-range promoted application of the TAVI.

With regard to the adjustment factor, there are mainly two existing methods of calculating $f(\Delta)$: optimization matching and optimization of extrema. The algorithm of optimization matching includes the following calculation steps: (1) image classification, i.e., dividing a shady slope and a sunny slope of a mountain in a remote sensing image and selecting a typical sample region; (2) object identification, i.e., verifying the homogeneity of vegetation of the shady slope and the sunny slope by means of ground survey data, on-the-spot investigation data, aerial photography data, high-resolution image data of GoogleEarth or the like, and identifying the consistent or similar vegetation areas of the shady slope and the sunny slope of the typical sample region; and (3) optimal matching, i.e., increasing $f(\Delta)$ in sequence from 0, investigating the changes in the vegetation index values of the TAVI in the consistent vegetation areas of the shady slope and the sunny slope of the typical sample region, and determining the optimal result of $f(\Delta)$ when the two are equal. The algorithm of optimization of extrema includes the following steps: (1) image classification, i.e., dividing a shady slope and a sunny slope of a mountain in a remote sensing image and selecting a typical sample region; calculating the extrema, i.e., calculating the maximum MTAVIshady of the TAVI of the shady slope area and the maximum MTAVIsunny of the TAVI of the sunny slope area; and (3) iterative optimization, i.e., increasing $f(\Delta)$ in sequence from 0, and obtaining the optimum value of $f(\Delta)$ when the conditions of the formula (2-3) are satisfied.

$$|M_{TAVIshady} - M_{TAVIsunny}| \leq \varepsilon, \varepsilon \to 0, f(\Delta) = 0 \sim \infty \quad (2\text{-}3)$$

The above two methods of calculating $f(\Delta)$ can effectively dilute the effects of topography on mountainous vegetation information with no need for support of data such as DEM; but the two optimization algorithms are relatively weak in physical significance because they depend on considerable experience and both require classification of a remote sensing image. In addition, the algorithm of optimization matching further needs support of ground data and the like, and the algorithm of optimization of extrema is prone to local optimization rather than global optimization. All of these limit the automation application level of the TAVI and are not good for the large-range promoted application of the TAVI.

BRIEF SUMMARY OF THE INVENTION

In view of this, an objective of the present invention is to provide a method of calculating a TAVI based on a band ratio model and a solar altitude angle. According to the method, a new, more stable SVI is constructed based on the basic principle of the band ratio model and RVI is preferred for combinational calculation with the new SVI, so that the TAVI algorithm can be more accurate and more convenient in application. What is more, a new algorithm of an adjustment factor f(Δ) based on a solar altitude angle is proposed, which does not need DEM data and remote sensing image classification, and is independent of ground survey data with practical physical significance, and has Important scientific significance and economic value for large-range application promotion of the TAVI for accurate inversion of the vegetation information of complex topographic mountainous areas.

To achieve the above objective, the present invention employs the following technical solution: a method of calculating a TAVI based on a band ratio model and a solar altitude angle which includes the following steps: step S1, preprocessing a remote sensing image and generating apparent reflectance data from the image by performing radiation correction on the remote sensing image; step S2, determining the apparent reflectance data of a red band and a near-infrared band of the remote sensing image, and analyzing whether the reflectance values of the mountainous vegetation are reasonable at the two bands to decide whether the image is normally available; step S3, calculating a Shadow Vegetation Index (SVI) using the following formula:

$$SVI = \frac{1}{B_r} \quad (3\text{-}1)$$

where SVI is the shadow vegetation index, and $B_r$ is the apparent reflectance data of the red band of the remote sensing image;

step S4, constructing a TAVI combinational algorithm, as specifically shown below:

$$TAVI = RVI + f(\Delta) \cdot SVI = \frac{B_{ir}}{B_r} + f(\Delta) \cdot \frac{1}{B_r} \quad (3\text{-}2)$$

where TAVI is the topography adjusted vegetation index; RVI is the ratio vegetation index; f(Δ) is an adjustment factor; $B_{ir}$ is the apparent reflectance data of the near-infrared band of the remote sensing image, and $B_r$ is the apparent reflectance data of the red band of the remote sensing image;

step S5, reading a solar altitude angle during a pass of a satellite from a header file of the remote sensing image and calculating f(Δ) by the following formula:

$$f(\Delta) = s - \sin(\alpha) \quad (3\text{-}3)$$

where s is a sensor parameter, and α is the solar altitude angle; and step S6, obtaining the mountainous anti-topographic effect vegetation index information by substituting the f(Δ) calculation result of the formula (3-3) into the formula (3-2).

The present invention has the following advantages when compared to the prior art:

1. More definite physical significance and simpler calculation: the new TAVI combinational algorithm is composed of two submodels RVI and SVI, both of which can meet the requirements of the band ratio model and are simple and similar in form. Moreover, the two submodels may have a better band ratio physical significance footing because their denominators are both red-band data of a remote sensing image. Moreover, the adjustment factor f(Δ) is calculated with a solar altitude angle, which may have definite physical significance. Additionally, the new method of calculating a TAVI is simpler in overall calculation flow, allowing a great improvement in the automation level of TAVI application.

2. Significant topographic correction results: the method of calculating a TAVI determined in the present invention ensures that the interference of the topographic effects with the vegetation information can be effectively eliminated by the TAVI. By utilizing Landsat multispectral remote sensing image data of different time phases in FIG. 1 of a research area (including Ladsat5 TM and Ladsat8 OLI image data), it indicates that the present invention can ensure that the mean values of the absolute values of the correlation coefficients for TAVIs of the Ladsat5 TM and Ladsat8 OLI Images of different time phases and cosine values (cosi) of solar incident angles are lower than 0.1 (table 1). That is, the TAVI is superior to other common vegetation indices and even better in results than the NDVI of the DEM-based C correction image calculation (FIG. 1).

The research area in FIG. 1 ranges in east longitude from 119°25'7" to 119°31'27", and in northern latitude from 26°6'35" to 26°12'15", and the RVI, NDVI, NDVI (C correction), and correlation coefficient for the TAVIs and cosine values (cosi) of the solar incident angles are 0.561, 0.524, 0.119 and 0.049, respectively.

TABLE 1

Comparison between f(Δ) adjustment factor calculation results of the Landsat data of different time phases and anti-topographic effects of the TAVIs

| Sensor | Time of Pass (Year/Month/Day) | Solar Altitude Angle | f(Δ) | r (RVI) | r (NDVI) | r (TAV1) | \|r\| (TAVI) |
|---|---|---|---|---|---|---|---|
| Landsat 5 | 1994 May 12 | 59.23 | 0.041 | 0.184 | 0.121 | 0.091 | 0.091 |
|  | 1996 Dec. 11 | 32.73 | 0.359 | 0.739 | 0.727 | 0.035 | 0.035 |
|  | 2000 Jun. 29 | 62.97 | 0.009 | 0.09 | 0.028 | 0.073 | 0.073 |
|  | 2001 Apr. 13 | 58.47 | 0.048 | 0.209 | 0.164 | 0.116 | 0.116 |
|  | 2001 Oct. 22 | 46.15 | 0.179 | 0.542 | 0.427 | 0.093 | 0.093 |
|  | 2003 Jan. 13 | 33.22 | 0.352 | 0.63 | 0.611 | −0.096 | 0.096 |
|  | Mean Value | 48.80 | 0.165 | 0.399 | 0.346 | 0.052 | 0.084 |
| Landsat 8 | 2013 Jul. 3 | 68.48 | 0.270 | 0.214 | 0.207 | 0.094 | 0.094 |
|  | 2013 Aug. 4 | 66.18 | 0.285 | 0.227 | 0.175 | 0.044 | 0.044 |

TABLE 1-continued

Comparison between $f(\Delta)$ adjustment factor calculation results of the
Landsat data of different time phases and anti-topographic effects of the TAVIs

| Sensor | Time of Pass (Year/Month/Day) | Solar Altitude Angle | $f(\Delta)$ | r (RVI) | r (NDVI) | r (TAV1) | \|r\| (TAVI) |
|---|---|---|---|---|---|---|---|
| | 2013 Oct. 23 | 48.60 | 0.450 | 0.518 | 0.325 | −0.033 | 0.033 |
| | 2014 Dec. 13 | 36.85 | 0.600 | 6.668 | 0.610 | 0.049 | 0.049 |
| | 2015 Sep. 27 | 56.03 | 0.371 | 0.434 | 0.269 | 0.079 | 0.079 |
| | 2016 Jun. 25 | 68.43 | 0.270 | 0.123 | 0.147 | 0.018 | 0.018 |
| | Mean Value | 57.43 | 0.374 | 0.364 | 0.289 | 0.042 | 0.053 |

3. Low data requirements and low costs: the present invention only needs the band data and solar altitude angle data carried in a remote sensing image itself with no need for the support of DEM data, ground survey data, on-the-spot investigation data or the like, thereby minimizing the data costs and the time costs.

4. It may also have an atmospheric correction result. Since SVI is the inverse transformation of red-band data and the information from vegetation regions that is weakened under the topographic effects in a remote sensing image will be compensated for (similar to the dark dense vegetation algorithm) to different extents, the new TAVI combinational algorithm has an atmospheric correction result to a certain extent.

5. Wide applicability: the new TAVI combination algorithm may be applied to apparent reflectance data, and may also be adapted to radiance value data and DN value data. This provides a new important technical means for some sensors lacking ground calibration parameters in accurate monitoring of a mountainous area's vegetation Information.

DETAILED DESCRIPTION OF THE INVENTION

The present invention will be further described below in conjunction with the accompanying drawings and an embodiment.

Figure 1:
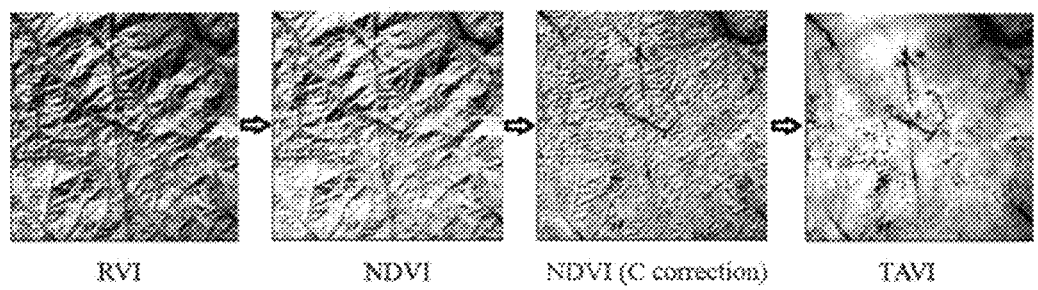
FIG. 1 is a schematic diagram of an image comparison in a research area in the present invention.
Figure 2:
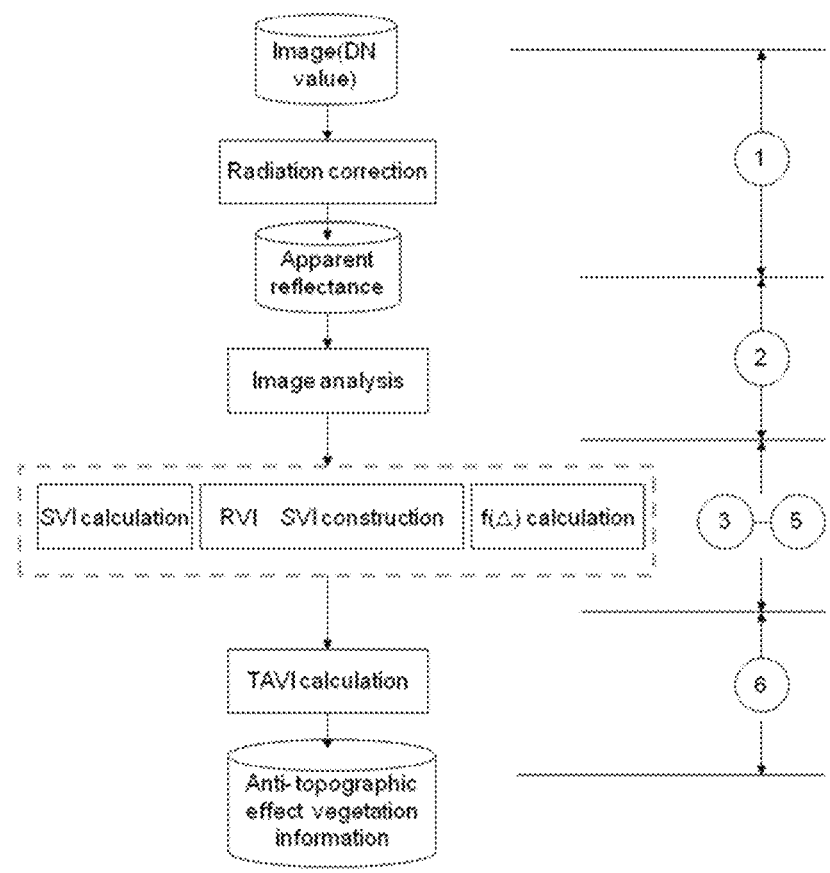
FIG. 2 is a schematic technical flow diagram of the present invention.

Referring to FIG. 2, the present disclosure provides a method of calculating a Topography Adjusted Vegetation Index (TAVI) based on a band ratio model and a solar altitude angle. The method includes the following steps.

At step S1, image preprocessing is performed, which specifically includes: performing radiation correction on a multi-spectral remote sensing image to generate apparent reflectance data of the image.

At step S2, the quality of the image is analyzed, which specifically includes: determining the apparent reflectance data of a red band and a near-infrared band of the remote sensing image (calculating mean values, mid-values, variances and other indices of the two bands) and analyzing whether the reflectance of mountainous vegetation is reasonable at the two bands to decide whether the image is normally available.

At step S3, a Shadow Vegetation Index (SVI) is calculated using the following formula:

$$SVI = \frac{1}{B_r} \quad (4\text{-}1)$$

where SVI is the shadow vegetation index, and $B_r$ is the apparent reflectance data of the red band of the remote sensing image.

At step S4, a TAVI combinational algorithm is constructed, as specifically shown below:

$$TAVI = RVI + f(\Delta) \cdot SVI = \frac{B_{ir}}{B_r} + f(\Delta) \cdot \frac{1}{B_r} \quad (4\text{-}2)$$

where TAVI is the topography adjusted vegetation index; RVI is the ratio vegetation index; $f(\Delta)$ is an adjustment factor; $B_{ir}$ is the apparent reflectance data of the near-infrared band of the remote sensing image, and $B_r$ is the apparent reflectance data of the red band of the remote sensing image.

At step S5, the adjustment factor $f(\Delta)$ is calculated. A solar altitude angle during a pass of a satellite is read from a header file of the remote sensing image and $f(\Delta)$ is calculated by the following formula:

$$f(\Delta)=s-\sin(\alpha) \quad (4\text{-}3)$$

where s is a sensor parameter. In an embodiment of the present invention, s is set to 1 by default. The values of s may be slightly adjusted according to different sensors. The value of the Landsat 5 TM data is 0.9, and the value of Landsat 8 OLI is 1.2. $\alpha$ is the solar altitude angle.

At step S6, the TAVI information is calculated. Mountainous anti-topographic effect vegetation index information is obtained by substituting the $f(\Delta)$ calculation result of the formula (4-3) Into the formula (4-2).

The remote sensing image includes optical remote sensing image data.

The foregoing are descriptions of the preferred embodiment of the present invention, and any variations and modifications made within the application patent scope of the present invention shall all be encompassed in the scope of the present invention.

What is claimed is:

1. A method of calculating a Topography Adjusted Vegetation Index (TAVI) based on a band ratio model and a solar altitude angle, the method comprising the following steps:

step S1, preprocessing a remote sensing image and generating apparent reflectance data of the image by performing radiation correction on the remote sensing image;

step S2, determining the apparent reflectance data of a red band and a near-infrared band of the remote sensing image;

step S3, calculating a Shadow Vegetation Index (SVI) using the following formula:

$$SVI = \frac{1}{B_r} \qquad (1\text{-}1)$$

wherein SVI is the shadow vegetation index, and $B_r$ is the apparent reflectance data of the red band of the remote sensing image;

step S4, constructing a TAVI combinational algorithm, as specifically shown below:

$$TAVI = RVI + f(\Delta) \cdot SVI = \frac{B_{ir}}{B_r} + f(\Delta) \cdot \frac{1}{B_r} \qquad (1\text{-}2)$$

wherein TAVI is the topography adjusted vegetation index; RVI is the ratio vegetation index; $f(\Delta)$ is an adjustment factor; $B_{ir}$ is the apparent reflectance data of the near-infrared band of the remote sensing image, and $B_r$ is the apparent reflectance data of the red band of the remote sensing image;

step S5, reading a solar altitude angle during a pass of a satellite from a header file of the remote sensing image and calculating the $f(\Delta)$ by the following formula:

$$f(\Delta) = s - \sin(\alpha) \qquad (1\text{-}3)$$

wherein s is a sensor parameter, and $\alpha$ is the solar altitude angle; and step S6, obtaining mountainous anti-topographic effect vegetation index information by substituting the $f(\Delta)$ calculation result of the formula (1-3) into the formula (1-2).

2. The method of calculating a TAVI based on a band ratio model and a solar altitude angle according to claim 1, wherein the remote sensing image includes optical remote sensing image data.

3. The method of calculating a TAVI based on a band ratio model and a solar altitude angle according to claim 1, wherein s, which is the sensor parameter and is set to 1 by default.

4. The method of calculating a TAVI based on a band ratio model and a solar altitude angle according to claim 1, wherein the step S2 also comprises: calculating mean values, mid-values, variances of the red band and the near-infrared band.

* * * * *